United States Patent
Kim et al.

(10) Patent No.: US 8,064,064 B2
(45) Date of Patent: Nov. 22, 2011

(54) APPARATUS AND METHOD FOR OBTAINING IMAGES USING COHERENT ANTI-STOKES RAMAN SCATTERING

(75) Inventors: Dug Young Kim, Gwangju (KR); Seung Bum Cho, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 265 days.

(21) Appl. No.: 12/370,581

(22) Filed: Feb. 12, 2009

(65) Prior Publication Data

US 2009/0213370 A1    Aug. 27, 2009

(30) Foreign Application Priority Data

Feb. 27, 2008 (KR) .................. 10-2008-0017799

(51) Int. Cl.
*G01J 3/45* (2006.01)
(52) U.S. Cl. ...................... 356/451; 356/456
(58) Field of Classification Search .......... 356/301, 356/422, 435, 436, 451, 456, 484, 491, 517
See application file for complete search history.

(56) References Cited

U.S. PATENT DOCUMENTS

| 7,388,668 | B2 * | 6/2008 | Potma et al. | 356/451 |
| 7,573,577 | B2 * | 8/2009 | Martinez | 356/451 |
| 7,586,618 | B2 * | 9/2009 | Marks et al. | 356/451 |
| 7,667,848 | B2 * | 2/2010 | Lee et al. | 356/451 |
| 2008/0192260 | A1 * | 8/2008 | Seong et al. | 356/484 |

* cited by examiner

*Primary Examiner* — Michael A Lyons

(57) ABSTRACT

Disclosed is an apparatus and method for obtaining images using coherent anti-stokes Raman scattering. The apparatus for obtaining images using coherent anti-stokes Raman scattering according to the present invention comprises: a pump light source and a stokes light source that irradiate pump light and stokes light on a sample to generate anti-stokes light having anti-stokes frequency; a reference light source that generates reference light; and an image obtaining unit that obtains the images of the sample using a change in phase of the reference light due to a change in the refractive index of the sample in the vicinity of the anti-stokes frequency. Thereby, the present invention can provide the apparatus for obtaining images using coherent anti-stokes Raman scattering that is not affected by a non-resonant background signal phenomenon, strong resistance against noise even in a weak signal, and has excellent sensitivity and resolution.

16 Claims, 7 Drawing Sheets

[FIG. 1] (Prior Art)
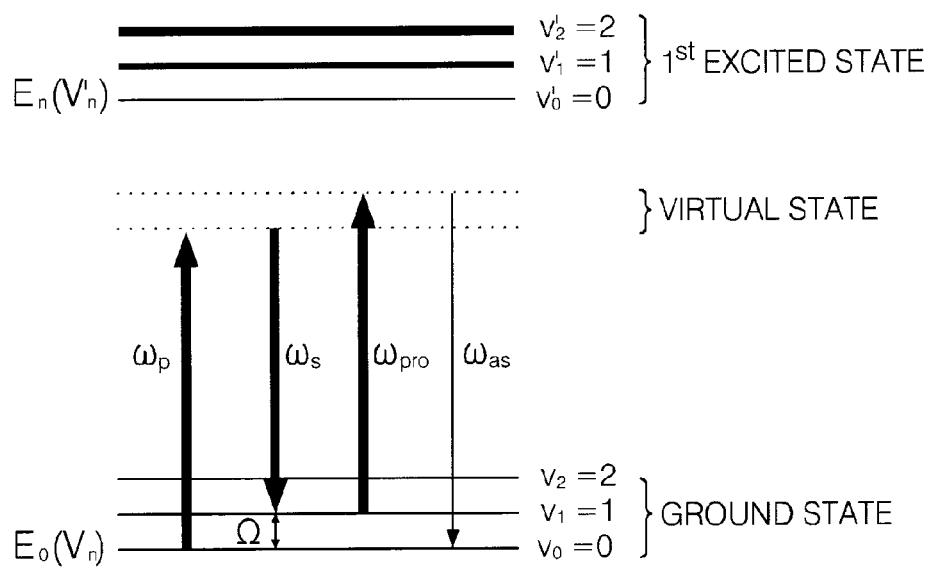

[FIG. 2]
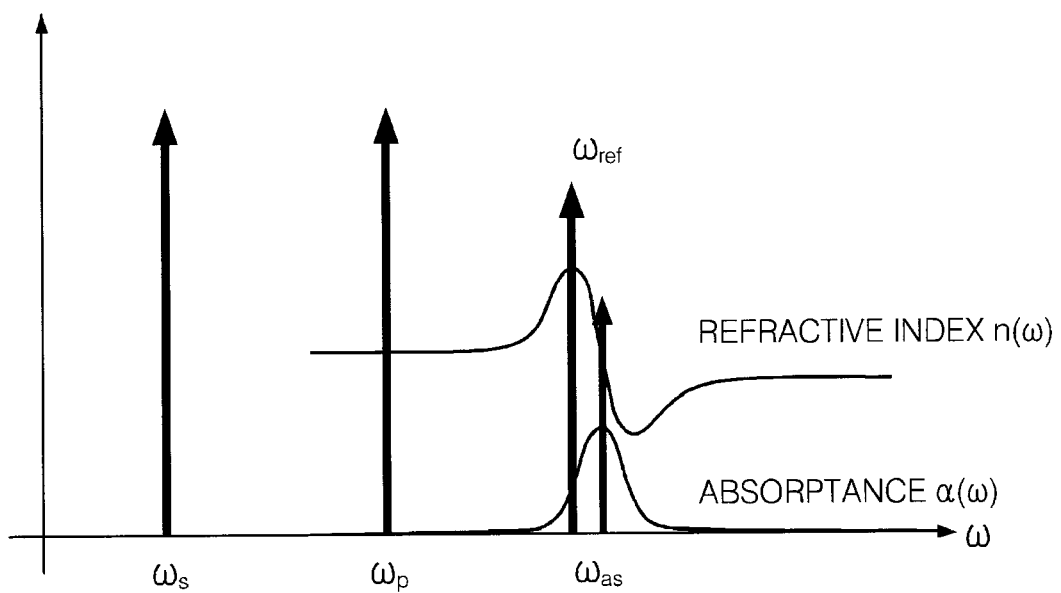

[FIG. 3]
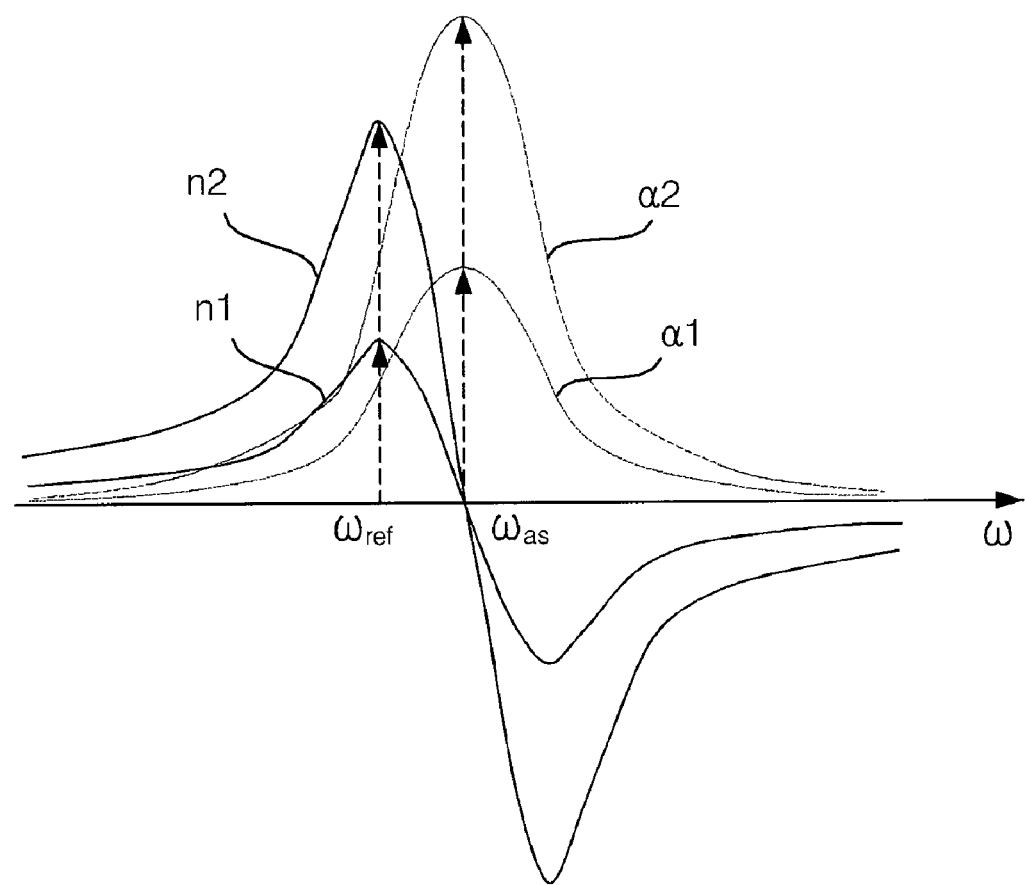

[FIG. 4]
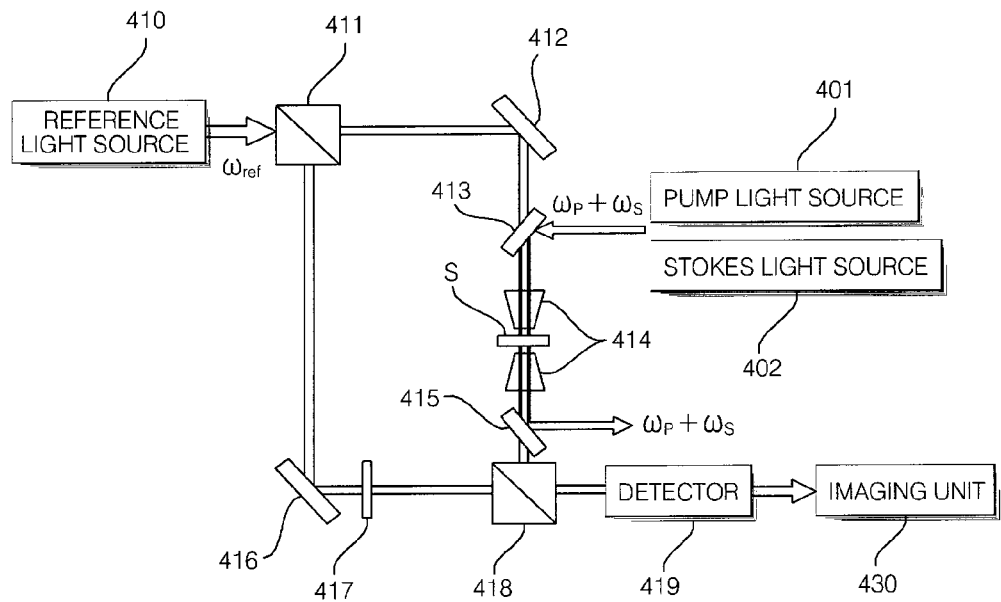
[FIG. 5]
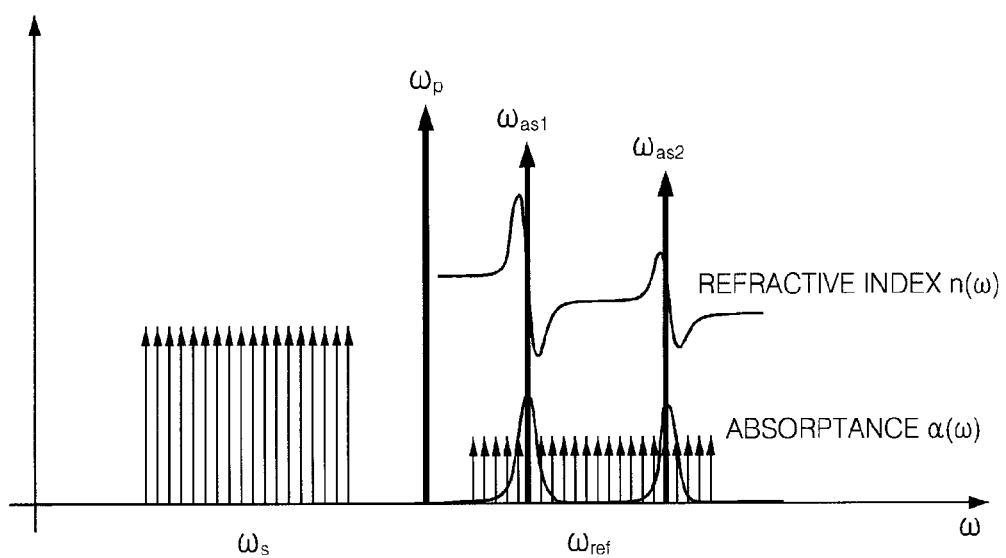

[FIG. 6]
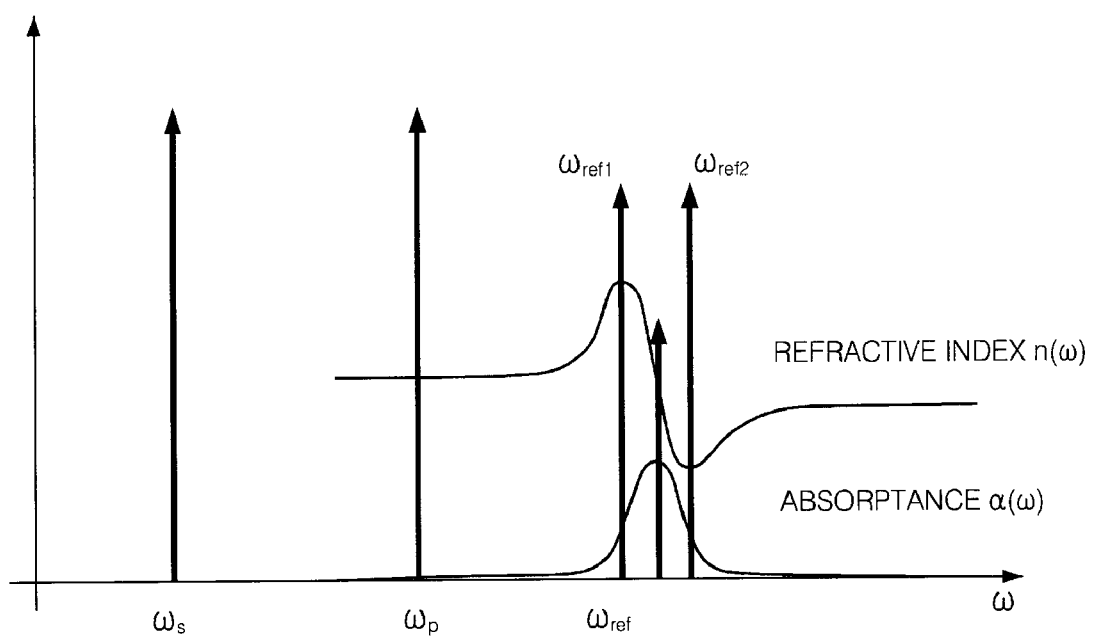

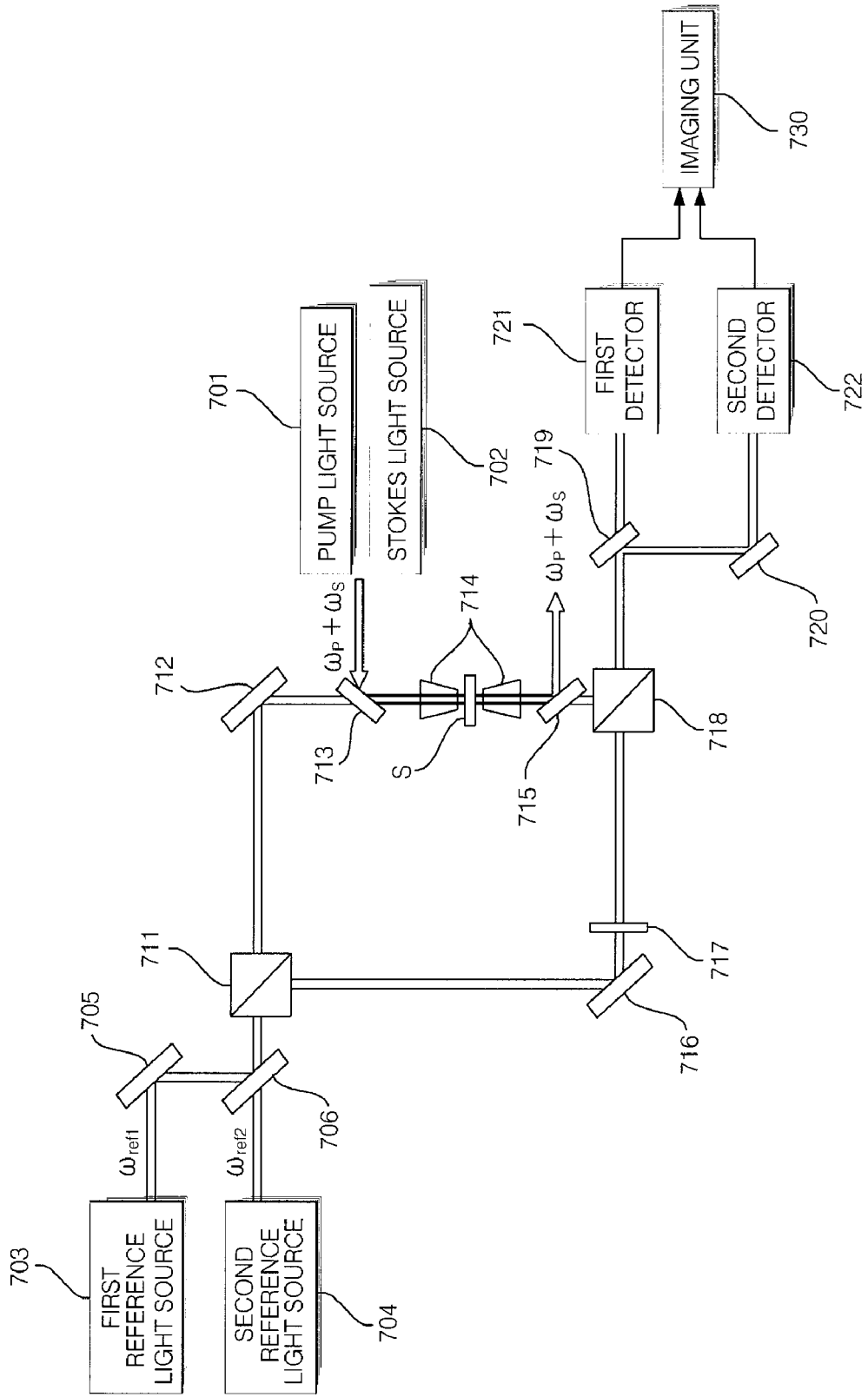

[FIG. 8]
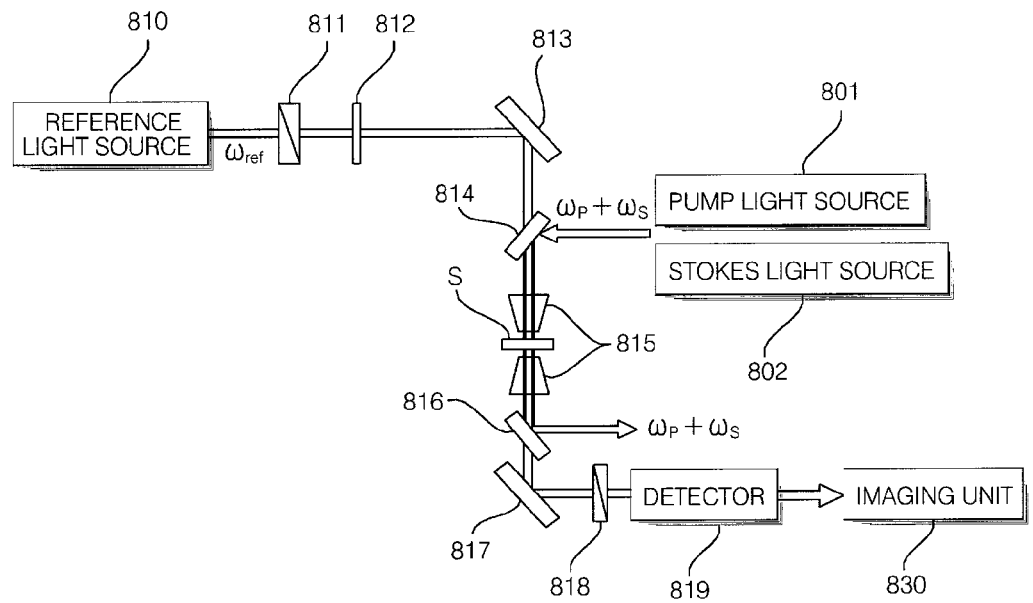
[FIG. 9]
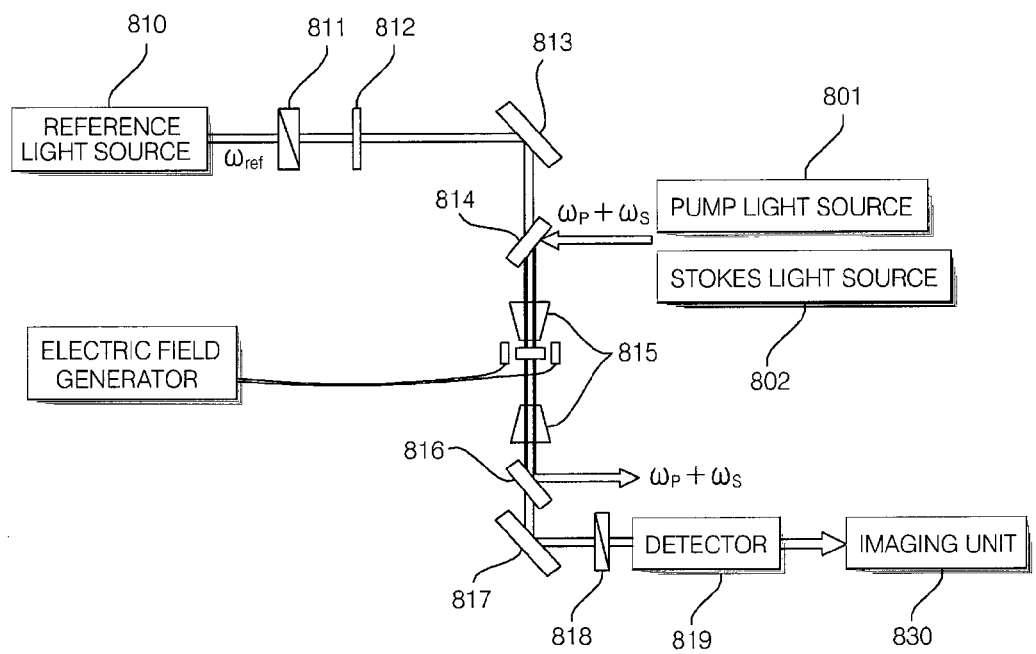

APPARATUS AND METHOD FOR OBTAINING IMAGES USING COHERENT ANTI-STOKES RAMAN SCATTERING

BACKGROUND OF THE INVENTION

1. Technical Field

The present invention relates to an apparatus and method for obtaining images to reveal structures and properties of materials and more particularity, to an apparatus and method for obtaining images using coherent anti-stokes Raman scattering.

2. Related Art

Raman spectroscopy is a phenomenon that scatters light having a wavelength different from that of monochromatic light input from a sample on which the monochromatic light is irradiated. Recently, the Raman spectroscopy tracks a change of a vibration mode together with infrared spectroscopy, such that it has established an independent area of learning that reveals structures and properties of molecules.

Even though the Raman spectroscopy was studied earlier than the infrared spectroscopy due to characteristic using Raman scattering light having weak strength, it has been slower in development. As a result, the frequency in the use of the Raman spectroscopy has been low until now. However, with the advent of a laser having improved output strength, the Raman spectroscopy is being developed rapidly. As a result, the use of the Raman spectroscopy is currently of interest for various applications.

Meanwhile, a fluorescent microscope is considered as the epochal technology in the field of cell biology due to the help of the development of various fluorescence probes, confocal detection, and three-dimensional imaging through multi-photon excitation. The fluorescent microscope irradiates a light source at a wavelength that can excite fluorescent molecules, which is known as the fluorescence probes naturally existing in the sample or artificially injected into the sample, on the sample. At this time, the sample emits fluorescence by absorbing the excitation light source and is observed using a filter that selectively transmits fluorescence. The fluorescent microscope is advantageous in that it has higher resolution than a general optical microscope. However, since the fluorescent microscope uses the fluorescence probes, it has problems in that it changes the sample to be measured and causes a photobleaching phenomenon.

A microscope using coherent anti-stokes Raman scattering (CARS) that inputs fixed/variable laser lights to Raman active media and measures spectrums of anti-stokes light obtained by a combination thereof has been widely used on the grounds that it has high sensitivity and is not affected by the media generating fluorescence.

FIG. 1 is an energy band diagram for explaining a generation principle of a general CARS signal. The CARS is a four wave mixing process that generates anti-stokes light by interacting pump light, stokes light, and probe light with a sample and uses two laser beams having different frequencies. A first laser beam serves as the stokes light ($\omega_s$) and a second laser beam serves as the pump light ($\omega_p$) and the probe light ($\omega_{pro}$). In other words, the frequency of $\omega_{pro}$ is identical with $\omega_p$. The electric field of the light is EP ($\omega_p$), ES ($\omega_s$), Epro ($\omega_{pro}$) (=EP ($\omega_p$)). If the laser beam is irradiated, electrons, which are in a ground state $v_0=0$ are first excited in a virtual state by the pump light ($\omega_p$) and most of the electrons are then transitioned into a level $v_1=1$ by the stokes light $\omega_s$. At this time, the inherent vibration frequency of the electrons becomes $\Omega$ by the resonant Raman scattering. After the electrons transitioned from $v_0=0$ to $v_0=1$ are back excited into a virtual state such as $\omega_p+\Omega$ by the probe light ($\omega_{pro}$), they emit the anti-stokes light having frequency $\omega_{as}=2\omega_p-\omega_s$ that satisfies energy conservation, that is, CARS signals, and are transitioned to the level $v_0=0$. The CARS microscope analyzes materials by measuring the strength of the CARS signal.

Since the CARS microscope as described above has the same resolution as the confocal microscope but does not use emission of a pigment, it does not change the sample. Further, since the CARS microscope uses Raman that corresponds to a vibration level of chemical species, it has an advantage in that it can select the chemical species. Moreover, the CARS microscope can obtain a very large signal as compared to spontaneous Raman scattering and because it has anti-stokes frequency different from the frequencies used by the two laser beams, the signal can be easily separated by using a filter, etc.

However, a representative disadvantage of the coherent anti-stokes Raman scattering is a non-resonant background signal phenomenon caused due to two-photon electronic resonance, which has been studied by [M. D. Duncan, J. Reintjes, and T. J. Manuccia, "Scanning coherent anti-Stokes Raman microscope," Opt. Lett. 7, 350-352, 1982]. It was found that any two-photon-enhanced background phenomenon exceeding the resonant vibration signal is generated due to the use of visible light. In a study by [A. Zumbusch, G. R. Holtom, and X. S. Xie, "Three-dimensional vibrational imaging by coherent anti-Stokes Raman scattering," Phys. Rev. Lett. 82, 4142-4145, 1999.], it was found that two-photon electronic resonance is prevented and sensitivity increase, by using near-infrared light. Thereafter, with the development of the coherent anti-stokes Raman scattering spectrometer, several methods were used for reducing the non-resonant background signal.

However, even though there are many problems in the conventional technologies associated with the CARS, these technologies all detected the strength of the CARS signal and directly analyzed them. As a result, these technologies focused on the difference between the CARS signal and the non-resonant background signal, such that many problems occurred. In particular, a method focusing on the reduction of the non-resonant background signal weakens the strength of light to be detected, such that there is a need for a high-specification photo detector in order to detect the signal having weak strength without noise. Further, since the method directly analyzes the signal to be detected by the strength of signal, it has limitations in sensitivity, resolution, accuracy, etc.

SUMMARY OF THE INVENTION

It is an object of the present invention to provide an apparatus for obtaining images using coherent anti-stokes Raman scattering, which is not affected by a non-resonant background signal phenomenon, has strong resistance against noise even in a weak signal, and has excellent sensitivity and resolution.

It is another object of the present invention to a method for obtaining images using coherent anti-stokes Raman scattering, which is not affected by a non-resonant background signal phenomenon, has strong resistance against noise even in a weak signal, and has excellent sensitivity and resolution.

In order to achieve the above object, there is provided an apparatus for obtaining images using coherent anti-stokes Raman scattering according to the present invention, comprising: a pump light source and a stokes light source that irradiate pump light and stokes light on a sample to generate anti-stokes light having anti-stokes frequency; a reference light source that generates reference light; and an image obtaining unit that obtains the images of the sample using a change in phase of the reference light due to a change in the refractive index of the sample in the vicinity of the anti-stokes frequency.

Preferably, the reference light has higher or lower frequency by a predetermined magnitude than the anti-stokes frequency.

Further, the image obtaining unit includes a unit that splits a path to a first path passing through the sample and a second path not passing through the sample and propagates a reference light to the first and second paths and may obtain the images of the sample using an interference phenomenon due to a phase difference between the reference light passing through the first path and the reference light passing through the second path.

Also, the reference light source includes a first reference light source and a second light source each generating first reference light having higher frequency by predetermined magnitude than the anti-stokes frequency and second reference light having lower frequency by a predetermined magnitude than the anti-stokes frequency, and the image obtaining unit includes a unit that splits a path into the first path passing through the sample and the second path not passing through the sample and propagates each of the first and second reference lights to the first and second paths and may obtain the images of the sample using a phase difference between the first reference light passing through the first path and the first reference light passing through the second path and a phase difference between the second reference light passing through the first path and the second reference light passing through the second path together.

In addition, the stokes light source generates stokes light having a broad frequency band to generate anti-stokes light having a plurality of anti-stokes frequencies, the reference light source generates reference light having a broad frequency band, the image obtaining unit may obtain the images of the sample using a change in phase of the reference light due to the change in refractive index of the sample in the vicinity of each of the plurality of anti-strokes frequencies.

In order to achieve the above object, there is provided an apparatus for obtaining images using coherent anti-stokes Raman scattering according to the present invention, comprising: a pump light source and a stokes light source that irradiate pump light and stokes light on a sample to generate anti-stokes light having anti-stokes frequency; a reference light source that generates reference light; and an image obtaining unit that obtains the images of the sample using the change in birefringence of the sample in the vicinity of the anti-stokes frequency.

The image obtaining unit may include a first polarizer that is installed at a position before the reference light propagated to paths passes through the sample and a second polarizer that is installed at a position before the reference light passes through the sample and has an optical axis in a direction different from the first polarizer.

Further, the image obtaining unit may further include an electromagnetic field generator that applies electric field or magnetic field to the sample.

In order to achieve another object, there is provided a method for obtaining images using coherent anti-stokes Raman scattering according to the present invention, comprising: (a) irradiating pump light and stokes light on a sample to generate anti-stokes light having anti-stokes frequency; (b) generating reference light; and (c) obtaining the images of the sample using a change in phase of the reference light due to a change in refractive index of the sample in the vicinity of the anti-stokes frequency.

Step (c) may include c1) splitting a path into a first path passing through the sample and a second path not passing through the sample and propagating the reference light to the first and second paths, and c2) obtaining the images of the sample using an interference phenomenon due to a phase difference between the reference light passing through the first path and the reference light passing through the second path.

Also, step (b) may include generating first reference light having higher frequency by predetermined magnitude than the anti-stokes frequency and second reference light having lower frequency by predetermined magnitude than the anti-stokes frequency, and step (c) includes c1) splitting a path into the first path passing through the sample and the second path not passing through the sample and propagating each of the first and second reference lights to the first and second paths and c2) obtaining the images of the sample using a phase difference between the first reference light passing through the first path and the first reference light passing through the second path and a phase difference between the second reference light passing through the first path and the second reference light passing through the second path together.

Further, step (a) irradiates stokes light having a broad frequency band on the sample to generate anti-stokes light having a plurality of anti-stokes frequencies, step (b) generates the reference light having a broad frequency band, and step (c) may obtain the images of the sample using the change in phase of the reference light due to a change in refractive index of the sample in the vicinity of each of the plurality of anti-strokes frequencies.

In order to solve another object, there is provided a method for obtaining images using coherent anti-stokes Raman scattering according to the present invention, comprising: (a) irradiating pump light and stokes light on a sample to generate anti-stokes light having anti-stokes frequency; (b) generating reference light; and (c) obtaining the images of the sample using a change in birefringence of the sample in the vicinity of the anti-stokes frequency.

Step (c) includes (c1) analyzing polarizing property before the reference light passes through the sample and polarizing property after the reference light passes through the sample and measuring birefrigence of the sample, and (c2) imaging the measured results.

Moreover, the a method for obtaining images using coherent anti-stokes Raman scattering may further include applying electric field or magnetic field to the sample.

The present invention can provide the apparatus and method for obtaining images using coherent anti-stokes Raman scattering, which is not affected by a non-resonant background signal phenomenon, has strong resistance against noise even in a weak signal, and has excellent sensitivity and resolution.

BRIEF DESCRIPTION OF THE DRAWINGS

FIG. 1 is an energy band diagram for explaining a generation principle of a general CARS signal;

FIG. 2 is a graph for explaining the appearance of how the refractive index is changed in the vicinity of anti-stokes frequency due to coherent anti-stokes Raman scattering;

FIG. 3 is a graph showing in more detail a change in absorptance and refractive index;

FIG. 4 is a diagram showing a configuration of an apparatus for obtaining images using the coherent anti-stokes Raman scattering according to one embodiment of the present invention;

FIG. 5 is a graph showing appearance, absorptance, and refractive index of anti-stokes light generated when a frequency band of stokes light is broad;

FIG. 6 is a graph for explaining an embodiment using two reference lights together in another embodiment of the present invention;

FIG. 7 is a diagram showing a configuration of an apparatus for obtaining images using coherent anti-stokes Raman scattering according to another embodiment of the present invention;

FIG. 8 is a diagram showing a configuration of an apparatus for obtaining images using coherent anti-stokes Raman scattering according to still another embodiment of the present invention; and FIG. 9 is a diagram showing a configuration of an apparatus for obtaining images using coherent anti-stokes Raman scattering according to still another embodiment of the present invention.

DESCRIPTION OF THE PREFERRED EMBODIMENTS

Hereinafter, preferred embodiments of the present invention will be described in detail with reference to the accompanying drawings. First of all, we should note that in giving reference numerals to elements of each drawing, like reference numerals refer to like elements even though like elements are shown in different drawings. Further, in describing the present invention, well-known functions or constructions will not be described in detail since they may unnecessarily obscure the understanding of the present invention.

The present invention implements an apparatus and method for obtaining images that is not affected by a non-resonant background signal phenomenon and has strong resistance against noise even if signals are weak without measuring signal strength of anti-stokes light generated by coherent anti-stokes Raman scattering but indirectly using it. To this end, the apparatus and method for obtaining images according to the present invention uses a principle where refractive index of a sample is changed in the vicinity of anti-stroke frequency having the anti-stroke light generated by the coherent anti-stroke Raman scattering.

FIG. 2 is a graph for explaining the appearance of how the refractive index is changed in the vicinity of anti-stokes frequency due to coherent anti-stokes Raman scattering. Referring to FIG. 2, $\omega_p$ represents frequency of pump light and $\omega_s$ represents frequency of stokes light. If the pump light and the stokes light are irradiated on a sample, the anti-stokes light having $\omega_{as}$ ($=2\omega_p-\omega_s$) is emitted from the sample. At this time, absorptance or emission of light is generated in the vicinity of the anti-stokes frequency, such that the absorptance $\alpha$ (or emission rate) is changed. Absorptance $n(\alpha)$ of light according to frequency in the vicinity of $\omega_{as}$ is shown in FIG. 2. The change in absorptance accompanies the change in refractive index. The change in absorptance and the change in absorptance depend on the following equation that is referred to as Kramer-Kronig relation.

$$\Delta n(\omega') = \frac{c}{\pi} P \int_0^\infty \frac{\Delta a(\omega) \, d\omega}{\omega^2 - \omega'^2} \quad \text{[Equation 1]}$$

where c is any constant and P means Cauchy principal value.

Refractive index n ($\omega$) according to the relation between the absorptance and the refractive index is shown in FIG. 2. As shown in FIG. 2, the refractive index is changed most in the vicinity of $\omega_{as}$.

FIG. 3 is a graph showing in more detail a change in absorptance and refractive index. Referring to FIG. 3, a refractive index graph $n_1$ corresponding to an absorptance graph $\alpha_1$ is shown in FIG. 3. As shown in FIG. 3, the most change in refractive index is at lower or higher frequency by a predetermined frequency in the vicinity of $\omega_{as}$. Also, it can be appreciated that as the change in absorptance is large based on $\omega_{as}$, the change in refractive index becomes larger in the vicinity of $\omega_{as}$.

FIG. 4 is a diagram showing a configuration of an apparatus for obtaining images using the coherent anti-stokes Raman scattering according to one embodiment of the present invention. Referring to FIG. 4, the apparatus for obtaining images according to the embodiment includes a pump light source 401 and a stokes light source 402 that generate pump light and stokes light irradiated on the sample to generate anti-stokes light having anti-stokes frequency, a reference light source 410 that generates reference light, and as shown in FIG. 4, an image obtaining unit that obtains images of the sample using the change in phase of the reference light due to the change in refractive index of the sample in the vicinity of the anti-stroke frequency. As the pump light source 401 and the stokes light source 402, a pulse type laser light source is used.

With the embodiment, the frequency $\omega_{ref}$ of the reference light has higher or lower frequency by a predetermined magnitude than the anti-stokes frequency $\omega_{as}$. At this time, it is preferable to have frequency corresponding to a point where the change in the refractive index is largest. For example, as shown in FIGS. 1 and 2, the frequency corresponding to the point where the change in refractive index is largest, that is, lower frequency by the predetermined magnitude than $\omega_{as}$ as the frequency of the reference light $\omega_{ref}$. Of course, it may use the higher frequency by the predetermined magnitude than $\omega_{as}$ as the frequency of the reference light.

Hereinafter, an operation of the apparatus for obtaining images according to the embodiment shown in FIG. 4 will be described. The pump light source 401 and the stokes light source 402 each generates the pump light at the frequency $\omega_p$ and the stokes light at the frequency $\omega_s$ and the pump light and the stokes light are reflected from a first dichroic reflector 413 and are irradiated on the sample S. In the sample, the anti-stokes light is generated due to the coherent anti-stokes Raman scattering. And, the pump light and the stokes light are reflected from a second dichroic reflector 415 and emitted to the outside. The first dichroic reflector 413 and the second dichroic reflector 415 perform a function of filtering the pump light and the stokes light by reflecting the pump light at the frequency $\omega_p$ and the stokes light at the frequency $\omega_s$ and passing through the reference light at the frequency $\omega_{ref}$.

The reference light source 410 generates the reference light having the frequency $\omega_{ref}$. The reference light is split into a first path passing through the sample S and a second path not passing through the sample S by a first optical splitter 411. At this time, the reference light split into the first path is reflected from the first reflector 412 and passes through the first dichroic reflector 413 and then passes through the sample S. At this time, the reference light can be magnified by a microscope object lens 414. As described above, in the sample S, since the change in the refractive index occurs in the vicinity of the anti-stokes frequency due to the coherent anti-stokes scattering, the reference light passing through the sample is subjected to the phase change. This reference light is incident to a second optical splitter 418.

The reference light split into the second path is reflected from the second reflector 416 and is incident to the second optical splitter 418. At this time, in order to maximize the interference pattern, a variable wavelength plate 417 may be disposed at the path of the reference light.

There is a phase difference between the reference light propagated to the first path passing through the sample and the reference light propagated to the second path not passing through the sample. Therefore, the interference phenomenon occurs after the reference light passes through the second optical splitter 418. The detector 419 detects signals due to the interference phenomenon and the detected signal is transferred to an imaging unit 430. As the detector 419, for example, a charge coupled device can be used. The imaging unit 430 analyzes the detected signal, images it, and outputs it through a display (not shown), etc.

In the above-mentioned embodiment, in order to change a relative length of the path between the reference light propagated to the first path and the reference light propagated to the second path, each component, for example, a transfer device, which transfers the first optical splitter 411, the first and second reflectors 412 and 416, and the like, may be installed.

Further, as a modified embodiment of the above-mentioned embodiment, a pulse type laser light source as the pump light source 401 is used and a broadband light source having a broad frequency band instead of a single frequency of a pulse type laser light source as the stokes light source 402, for example, an LED light source is used.

FIG. 5 is a graph showing appearance, absorptance, and refractive index of anti-stokes light generated when a frequency band of stokes light is broad. As shown in FIG. 5, when the anti-stokes light has a sufficient broad frequency band, the coherent anti-stokes Raman scattering is generated at a plurality of frequencies to generate the anti-stokes light having a plurality of anti-stokes frequencies $\omega_{asi}$ and $\omega_{as2}$. Therefore, the images of the sample can be obtained using the change in phase of the reference light due to the change in the refractive index of the sample at each frequency. To this end, in the present embodiment, the reference light also uses the reference light having the broad frequency band. As the detector 419, a device capable of detecting the signals generated due to the interference phenomenon at several frequency bands is used. For example, an arrayed detector or a CCD array, etc., may be used.

FIG. 6 is a graph for explaining an embodiment using two reference lights, that is, two reference lights each having a lower frequency $\omega_{ref1}$ by the predetermined magnitude than the anti-stokes frequency $\omega_{as}$ and higher frequency $\omega_{ref2}$ by the predetermined magnitude than the anti-stokes frequency $\omega_{as}$ together as another embodiment of the present invention. As shown in FIG. 6, the sign of the refractive index at $\omega_{ref1}$ and the refractive index at $\omega_{ref2}$ is opposite to each other based on the refractive index at the anti-stokes frequency $\omega_{as}$. Therefore, the noise at the time of measuring the change in strength of the light source, etc. can be reduced by using the difference between the refractive indexes at two frequencies.

FIG. 7 is a diagram showing a configuration of an apparatus for obtaining images using coherent anti-stokes Raman scattering according to another embodiment of the present invention and is a configuration diagram showing an embodiment using two reference lights each having two frequencies of $\omega_{ref1}$ and $\omega_{ref2}$.

Referring to FIG. 7, an apparatus for obtaining images according to the present embodiment includes a pump light source 701 and a stokes light source 702 that generate pump light and stokes light irradiated on the sample to generate anti-stokes light having anti-stokes frequency, a first reference light source 703 and a second reference light source 704 that generate first reference light at $\omega_{ref1}$ and second reference light at $\omega_{ref2}$, a unit that splits a path into the first path passing through the sample S and the second path not passing through the sample S and propagates each of the first and second reference lights to the first and second paths and an image obtaining unit that obtain the images of the sample using a phase difference between the first reference light passing through the first path and the first reference light passing through the second path and a phase difference between the second reference light passing through the first path and the second reference light passing through the second path together.

Hereinafter, the operation of the apparatus for obtaining images according to the embodiment shown in FIG. 7 will be described. The pump light source 701 and the stokes light source 702 each generates the pump light at the frequency $\omega_p$ and the stokes light at the frequency $\omega_s$ and the pump light and the stokes light are reflected from a second dichroic reflector 713 and are irradiated on the sample S. In the sample S, the anti-stroke light is generated due to the coherent anti-stokes Raman scattering. The pump light and the stokes light are reflected from a third dichroic reflector 715 and are discharged to the outside. The second dichroic reflector 713 and the third dichroic reflector 715 reflect the pump light at the frequency $\omega_p$ and the stokes light at the frequency $\omega_s$ while performing as a filter for the pump light and the stokes light by passing through the pump light at the frequency $\omega_{ref1}$ and the stokes light at the frequency $\omega_{ref2}$.

The first reference light source 703 generates the first reference light having the frequency $\omega_{ref1}$. The first reference light is reflected from the first reflector 705 and the first dichroic reflector 706 and is incident on the first splitter 711, which is in turn split into two paths, where the first path passes through the sample S and the second path does not pass through the sample S.

The second reference light source 704 generates the second reference light having the frequency $\omega_{ref2}$. The second reference light passes through the first dichroic reflector 706 and is incident on the first splitter 711, which is in turn split into two paths, where the first path passes through the sample S and the second path does not pass through the sample S like the first reference light.

The first reference light and the second reference light split into the first path are reflected from the second reflector 712 and passes through the sample S via the second dichroic reflector 713. At this time, the reference light can be magnified by a microscope object lens 714. As described above, in the sample S, since the change in refractive index occurs in the vicinity of the anti-stokes frequency due to the coherent anti-stokes scattering, the reference light passing through the sample is subjected to the phase change. The first reference light and the second reference light passing through the sample are incident to a second optical splitter 718.

The first reference light and the second reference light split into the second path are reflected from a third reflector 716 and are incident to the second optical splitter 718. At this time, in order to maximize the interference pattern, a variable wavelength plate 717 may be disposed in the paths.

There is a phase difference between the first reference light propagated to the first path passing through the sample S and the second path that does not pass through the sample S. Therefore, after the first reference light passes through the second optical splitter 718, the interference phenomenon occurs. This interference is interference at the frequency $\omega_{ref1}$.

Likewise, there is a phase difference between the second reference light propagated to the first path passing through the sample S and the second reference light propagated to the second reference light not passing through the sample S. Therefore, after the second reference light passes through the second optical splitter 718, the interference phenomenon occurs. This interference is interference at the frequency $\omega_{ref2}$.

The third dichroic reflector 719 passes through the light at the frequency $\omega_{ref1}$ and reflects the light at the frequency $\omega_{ref1}$. Therefore, the first detector 721 detects the signals due to the interference phenomenon at the frequency $\omega_{ref1}$ area and the second detector 722 detects the signals due to the interference phenomenon at the frequency $\omega_{ref2}$ area reflected from a fourth reflector 720. The signals detected in each of the first detector 721 and the second detector 722 are input to an imaging unit 730. The imaging unit 730 images a difference between the signal detected in the first detector 721 and the signal detected in the second detector 722 and outputs it through the display (not shown) etc.

FIG. 8 is a diagram showing a configuration of an apparatus for obtaining images using coherent anti-stokes Raman scattering according to still another embodiment of the present invention. As described with reference to FIG. 2, when the refractive index is changed in the vicinity of the anti-stokes frequency upon generating the coherent anti-stroke Raman scattering, the change in birefringence is differently displayed according to directivity of the refractive index. With the embodiment, the images of the sample are obtained using the change in birefringence.

Referring to FIG. 8, an apparatus for obtaining images according to the present invention includes a pump light source 801 and a stokes light source 802 that generate pump light and stokes light irradiated on the sample to generate anti-stokes light having anti-stokes frequency, a reference light source 810 that generates reference light having higher or lower frequency by a predetermined magnitude than the anti-stroke frequency, and as shown in FIG. 8, an image obtaining unit that obtains images of the sample S using the change in polarizing state of the reference light due to the change in birefringence of the sample. As the pump light source 801 and the stokes light source 802, a pulse type laser light source is used.

The pump light source 801 and the stokes light source 802 each generates the pump light at the frequency $\omega_p$ and the stokes light at the frequency $\omega_s$ and the pump light and the stokes light are reflected from a first dichroic reflector 814 and are irradiated on the sample S. In the sample, the anti-stokes light is generated due to the coherent anti-stokes Raman scattering. And, the pump light and the stokes light are reflected from a second dichroic reflector 816 and emitted to the outside. The first dichroic reflector 814 and the second dichroic reflector 816 performs a function of filtering the pump light and the stokes light by reflecting the pump light at the frequency $\omega_p$ and the stokes light at the frequency $\omega_s$ and passing through the reference light at the frequency $\omega_{ref}$.

The reference light source 810 generates the reference light having the frequency $\omega_{ref}$. The reference light becomes light polarized in an optical axis direction owned by a first polarizer 811 after passing through the first polarizer 811. The polarized reference light passes through a variable wavelength plate 812 and then reflected from the first reflector 813, which is in turn irradiated on the sample S. At this time, the reference light can be magnified by a microscope object lens 815. The reference light passes through the sample S and the reflected from the second reflector 817. And, the reference light is incident on an optical axis in a different direction from the first polarizer 811, for example, a second polarizer 818 having the optical axis having a difference by 90°. A detector 819 detects the reference light passing through the second polarizer 818 and an imaging unit 830 analyzes polarizing property of the reference light before passing through the sample S and polarizing property of the reference light after passing through the sample S, measure the birefringence, images it, and outputs it through the display (not shown) etc.

FIG. 9 is a diagram showing a configuration of an apparatus for obtaining images using coherent anti-stokes Raman scattering according to still another embodiment of the present invention and shows an embodiment further including an electromagnetic generating unit 840 that applies electric field or magnetic field to the sample S in the apparatus for obtaining images. As shown in FIG. 9, if the electric field or the magnetic field is applied to the sample S, the coherent anti-stroke Raman scattering effect can be increased or reduced. Therefore, the change in birefringence due to the coherent anti-stokes Raman scattering can be controlled.

With the present invention, the images of the sample can be obtained by using the change in the refractive index or the change in birefringence in the vicinity of the anti-stokes frequency owned by the anti-stokes light without directly measuring the signal strength of the anti-stokes light generated by the coherent anti-stokes Raman scattering. Therefore, the present invention can implement the apparatus for obtaining images using coherent anti-stokes Raman scattering that is not affected by the non-resonant background signal phenomenon and has strong resistance against noise even if the signal is weak and has excellent sensitivity and resolution since the change in the refractive index has nothing to do with the signal strength Although the preferred embodiment of the present invention is described, it will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An apparatus for obtaining images using coherent anti-stokes Raman scattering comprising:
   a pump light source and a stokes light source that irradiate pump light and stokes light on a sample to generate anti-stokes light having anti-stokes frequency;
   a reference light source that generates reference light; and
   an image obtaining unit that obtains the images of the sample using a change in phase of the reference light due to a change in the refractive index of the sample in the vicinity of the anti-stokes frequency.

2. The apparatus for obtaining images according to claim 1, wherein the reference light has higher or lower frequency by a predetermined magnitude than the anti-stokes frequency.

3. The apparatus for obtaining images according to claim 1, wherein the image obtaining unit includes a unit that splits a path to a first path passing through the sample and a second path not passing through the sample and propagates a reference light to the first and second paths and obtains the images of the sample using an interference phenomenon due to a phase difference between the reference light passing through the first path and the reference light passing through the second path.

4. The apparatus for obtaining images according to claim 1, wherein the reference light source includes a first reference light source and a second light source each generating first reference light having higher frequency by predetermined magnitude than the anti-stokes frequency and second reference light having lower frequency by predetermined magnitude than the anti-stokes frequency, and the image obtaining unit includes a unit that splits a path into the first path passing through the sample and the second path not passing through the sample and propagates each of the first and second reference lights to the first and second paths and obtains the images of the sample using a phase difference between the first reference light passing through the first path and the first reference light passing through the second path and a phase difference between the second reference light passing through the first path and the second reference light passing through the second path together.

5. The apparatus for obtaining images according to claim 1, wherein the stokes light source generates stokes light having a broad frequency band to generate anti-stokes light having a plurality of anti-stokes frequencies, the reference light source generates reference light having a broad frequency band, and the image obtaining unit obtains the images of the sample using a change in phase of the reference light due to a change in the refractive index of the sample in the vicinity of each of the plurality of anti-strokes frequencies.

6. An apparatus for obtaining images using coherent anti-stokes Raman scattering comprising:

a pump light source and a stokes light source that irradiate pump light and stokes light on a sample to generate anti-stokes light having anti-stokes frequency;

a reference light source that generates reference light; and an image obtaining unit that obtains the images of the sample using a change in birefringence of the sample in the vicinity of the anti-stokes frequency.

7. The apparatus for obtaining images according to claim 6, wherein the image obtaining unit includes a first polarizer that is installed at a position before the reference light propagated to paths passes through the sample and a second polarizer that is installed at a position before the reference light passes through the sample and has an optical axis in a direction different from the first polarizer.

8. The apparatus for obtaining images according to claim 6, wherein the image obtaining unit further includes an electromagnetic field generator that applies electric field or magnetic field to the sample.

9. A method for obtaining images using coherent anti-stokes Raman scattering comprising:

(a) irradiating pump light and stokes light on a sample to generate anti-stokes light having anti-stokes frequency;

(b) generating reference light; and (c) obtaining the images of the sample using a change in phase of the reference light due to a change in refractive index of the sample in the vicinity of the anti-stokes frequency.

10. The method for obtaining images according to claim 9, wherein the reference light has higher or lower frequency by a predetermined magnitude than the anti-stokes frequency.

11. The method for obtaining images according to claim 9, wherein step (c) include:

c1) splitting a path into a first path passing through the sample and a second path not passing through the sample and propagating the reference light to the first and second paths; and c2) obtaining the images of the sample using an interference phenomenon due to a phase difference between the reference light passing through the first path and the reference light passing through the second path.

12. The method for obtaining images according to claim 9, wherein step (b) includes generating first reference light having higher frequency by a predetermined magnitude than the anti-stokes frequency and second reference light having lower frequency by a predetermined magnitude than the anti-stokes frequency, and step (c) includes, c1) splitting a path into the first path passing through the sample and the second path not passing through the sample and propagating each of the first and second reference lights to the first and second paths; and c2) obtaining the images of the sample using a phase difference between the first reference light passing through the first path and the first reference light passing through the second path and a phase difference between the second reference light passing through the first path and the second reference light passing through the second path together.

13. The method for obtaining images according to claim 9, wherein step (a) irradiates stokes light having a broad frequency band on the sample to generate anti-stokes light having a plurality of anti-stokes frequencies, step (b) generates the reference light having a broad frequency band, and step (c) obtains the images of the sample using a change in phase of the reference light due to a change in refractive index of the sample in the vicinity of each of the plurality of anti-strokes frequencies.

14. A method for obtaining images using coherent anti-stokes Raman scattering comprising:

(a) irradiating pump light and stokes light on a sample to generate anti-stokes light having anti-stokes frequency;

(b) generating reference light; and (c) obtaining the images of the sample using a change in birefringence of the sample in the vicinity of the anti-stokes frequency.

15. The method for obtaining images according to claim 14, wherein step (c) includes, (c1) analyzing polarizing property before the reference light passes through the sample and polarizing property after the reference light passes through the sample and measuring birefrigence of the sample, and (c2) imaging the measured results.

16. The method for obtaining images according to claim 14, further comprising electric field or magnetic field to the sample.

* * * * *